United States Patent [19]

Hwang

[11] Patent Number: 4,947,154

[45] Date of Patent: Aug. 7, 1990

[54] ALARM DEVICE FOR DRIPPING INJECTION

[76] Inventor: Feng-Lin Hwang, No. 21, Pa Te Rd., Chi Tu District, Keelung City, Taiwan

[21] Appl. No.: 393,728

[22] Filed: Aug. 15, 1989

[51] Int. Cl.$^5$ ............................................. G08B 21/00
[52] U.S. Cl. ................................. 340/624; 200/82 C; 604/254; 604/127; 128/DIG. 13
[58] Field of Search ............... 340/623, 624, 693, 618; 128/DIG. 13; 604/254, 127; 200/82 C

[56] References Cited

U.S. PATENT DOCUMENTS

| | | | |
|---|---|---|---|
| 3,942,526 | 3/1976 | Wilder et al. | 340/624 |
| 3,989,043 | 11/1976 | Dimeff | 604/254 |
| 4,244,364 | 1/1981 | Grushkin | 340/624 |
| 4,328,820 | 5/1982 | Serur | 604/254 |
| 4,449,976 | 5/1984 | Kamen | 604/254 |
| 4,769,007 | 9/1988 | Hsu | 604/127 |
| 4,794,379 | 12/1988 | Wang | 128/DIG. 13 |

Primary Examiner—Joseph A. Orsino
Assistant Examiner—Jill Jackson
Attorney, Agent, or Firm—Browdy and Neimark

[57] ABSTRACT

An alarm device for dripping injection comprising a floating barrel which vertically moves up or down according to fluid volume in the dripping liquid barrel, a touch switch and sealing means which are provided in the upper area of the lower part of dripping liquid barrel, a socket which is provided in the dripping liquid barrel lower part for connection to touch switch, and a power lead and plug provided by a separate action box or a patient room's call assembly to plug the socket. As the contained fluid is used near empty and the fluid volume in the dripping liquid barrel diminishes meantime, the floating barrel, when loosing support by the fluid volume, moves down and touches the touch switch with its own weight, thereby conducting open the separate action box or the patient room's call assembly to alarm nurses or hospital orderly to come to handle.

2 Claims, 3 Drawing Sheets

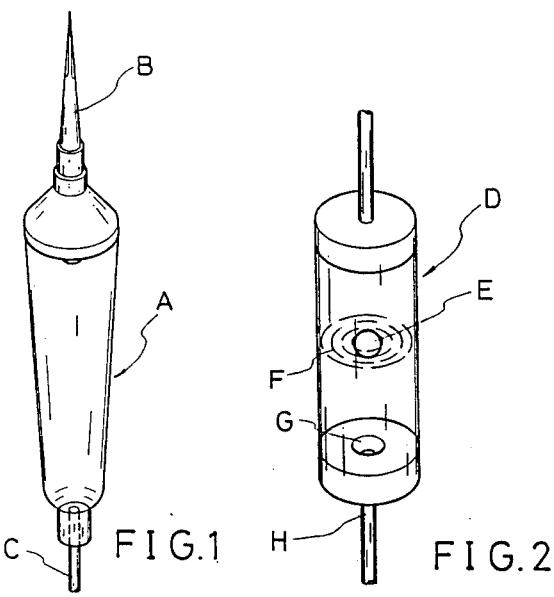
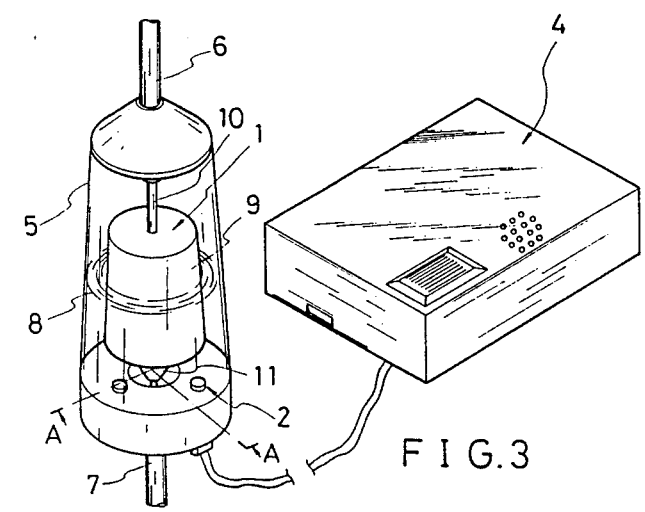

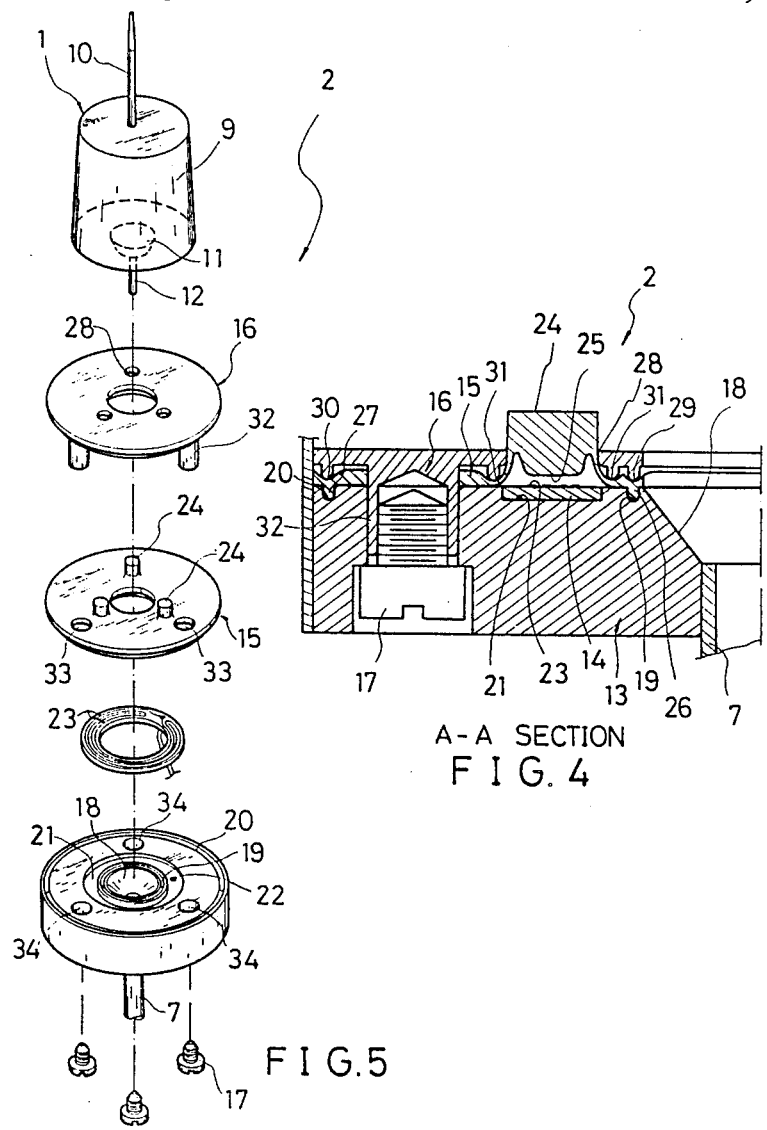

ALARM DEVICE FOR DRIPPING INJECTION

FIELD OF THE INVENTION

The present invention relates to an alarm device for dripping injection, and particularly to an alarm devicve applied in medical field that when a bottled injection fluid is near empty, the device can close the fluid passage automatically and sound alarm simultaneously to alert attendant or nurses to come to handle right away. Thus, not only medical quality could be enchanced but also patient's safety can be ensured.

BACKGROUND OF THE INVENTION

Dripping inejction usually takes some long hours to finish, so it is impossible for the nurses to take care of patient at bedside all the time. In general cases, nurses just leave away after dripping injection is arranged to begin and would come back to veiw the condition only occasionally. That easily causes the patient to grow psychological fear and complaint and is unable to take a full rest, since he or she may fear the air may enter to the blood vessel to cause danger at end of the dripping injection when nurse fails to come to handle timely.

FIG. 1 shows a conventionally used dripping liquid barrel A for dripping injection procedure. Dripping liquid barrel A is provided with a penetrating needle B for stabbing stopper into a fluid bottle (not shown in the figure) to guide the fluid drippingly thereinto, and has a flexible outlet pipe C connected to its bottom floor for fluid delivery. However, it has the sole function in reducing pressure for outlet pipe C. Still, if the injection needle (not shown in the figure) fails to be removed before fluid depletion, there would be danger of the air entrance into human body way of the injection needle. FIG. 2 shows an improved dripping liquid barrel D. Dripping liquid barrel D has a float ball E therein which can be supported to depart from fluid outlet G fluid by volume F, so that float ball E may come down to block outlet G, when loosing support of fluid volume F, to prevent air entrance into outlet pipe H. But, as a matter of fact, the bottom of dripping liquid barrel D is plane form for which reason float ball E will not necessarily land on outlet G as wished, and even if float ball E lands and block G, this sort of sealing is merely for the time being. It no doctor or nurse comes to handle in time, there would still be danger of air entrance into human body.

OBJECT OF THE INVENTION

The major object of the invention is to solve the problem above by providing an alarm device for dripping injection which has features:

1. A float barrel is provided, keeping vertical movement, and whose top having slanted degree can adjust the inlet quantity of the injection fluid. It is expected the inlet speed is highest when the dripping liquid barrel contains no fluid, and that the inlet speed becomes fixed when a predetermined fluid quantity is reached.

2. The mid bottom of the float barrel can assuringly block the fluid outlet and tightly seal it.

3. As injection fluid is near empty and the stuffing body of the float barrel mid bottom blocks and seals the fluid outlet, a touch switch around will be touched simultaneously which the conducts open power source of a pluggedly connected action box to send out alarming sounds and flashes for doctor or nurses to come to handle immediately.

4. Optionally, the touch switch could be pluggedly connected with call assembly of the patient room that would result in the same effect when its power source is conducted open.

SUMMARY OF THE INVENTION

An alarm device for dripping injection, comprising: a float barrel which can move vertically in a dripping liquid barrel, a touch switch and sealing means both of which are placed in the upper of the lower part of the dripping liquid barrel, a socket which is placed in the dripping liquid bottom part of connection to the touch switch, and an action box which has power lead and plug provided for plugged connection. As injection fluid is near empty and the fluid pool inside the dripping liquid barrel diminishes accordingly, the float barrel, when loosing buoyancy from fluid pool, is caused to come down to press the touch switch which then will conduct open power source of the pluggedly connected action box, so the buzzer and flasher therein are thus activated to generate alarming calls and flashes for doctor or nurses to come to handle right away.

BRIEF DESCRIPTION OF THE DRAWING

FIG. 1 shows construction of a conventionally used dripping liquid barrel in dripping injection procedure.

FIG. 2 shows construction of another conventionally used dripping liquid barrel in dripping injection procedure.

FIG. 3 is a perspective view of a preferred embodiment according to the invention.

FIG. 4 is an enlarged sectional view taken along A—A line of FIG. 3.

FIG. 5 is an exploded view of construction of FIG. 4.

SPECIFIC DESCRIPTION

Figure 7:
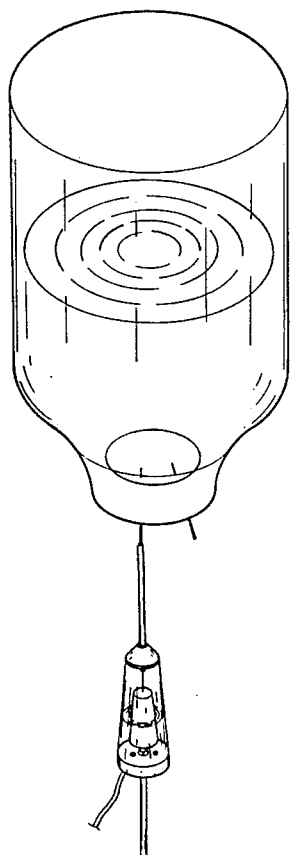
FIG. 7. shows this invention assembled with dripping injection instruments is ready for use.

Firstly referring to FIGS. 3–5, this invention comprises: float barrel 1 moving vertically in a dripping liquid barrel, touch switch 2 placed in the upper of the lower part of the dripping liquid barrel, socket 3 placed in the dripping liquid bottom part for connection to touch switch 3, and a separate action box 4 having power lead and plug provided for plugged connection. Float barrel 1, stringed between fluid inlet tube 6 and outlet tube 7 inside dripping liquid barrel 5, can move up or down vertically in accord with quantity of the fluid pool 8 therein, and is made up by barrel body 9, upper guide arm 10, stuffing body 11, and lower guide arm 12. Barrel body 9 is in cone or other proper form and hollow inside and is provided of a present buoyancy staying in fluid pool 8. Connected to barrel body top, upper guide arm 10, whose upper half is cone-shaped, is used to insert into fluid inlet tube 6 to guide barrel body 9 to make vertical up or down movement with collaboration of lower guide arm 12, and change of the cone-shaped part inserted in inlet tube 6 has function in adjustment of the inlet flow. Therefore, in control, the fluid 8 streaming into dripping liquid barrel 5 varies of speed from quick to slow and the inlet room is almost closed in the long run when the fluid quantity present in dripping liquid barrel 5 is reached. In the bottom center of barrel body 9, there are stuffing body 11 and lower guide arm 12 provided, so that as barrel body 9 descends because of shortage of fluid 8, stuffing body 11, under guide of lower guide arm 12, will go blocking the opening of outlet tube 7 finally. And at that time, bottom floor of barrel body 1 will touch touch switch 2 to cause action box 4 to generate action. The touch switch 2 comprises of seat block 13, PC board 14, buttoned sheet 15, press sheet 16, and locking screw 17 (as FIGS. 4 and 5 show). Seat bock 13, adapted to the dripping liquid barrel 5 bottom part therefore to be cylindric, is provided with opening 18 in its center as the outlet for outlet tube 7 to connect with; outside outlet opening 18, there are tow rings of raised fillisters 19, 20 concentrically cut out, and between the two rings is cut an annular concavity 21 of dimension adapted to PC board 14 for combining it gluedly or insertedly, and cavity 22 is provided for the passage of power lead connected to socket 3. PC board 14, annular in form, is provided with some copper foil circuits 23 going around on the board surface, any two of which if conducted open by button 24 will in turn conduct open power source of action box 4 which then is caused to taken action. On buttoned sheet 15, button 24, one or more than one set in number, made of resilient material (such as silicic rubber or general rubber), and thus take position by its resilient nature, so a proper small amount of pressure could overcome its resilience and make its touch point 25 in contact with the circuits 23 of PC board 14 so as to cause conduction therewithin. Touch point 25 has been glued with conductable carbon power. Buttoned sheet 15 has two annular rings of ridges 26, 27 provided on the bottom back face, which are in adaption to two annular rings of fillisters 19, 20, so to be able to well engage itself with annular rings of fillisters 19, 20 when settled on seat block 13, this way that PC board 14 can be sealed entirely to be water-tight. Press board 16, made of tough material, is provided with hole 28, same in number as button 24 for the button protrusion, on the board surface, and is provided with inner and outer packing washers 29, 30 and hole washer 31 on the bottom back face to press on resilient buttoned sheet 15 and, furthermore, three screw bolts 32 which pass through the hole 33 of buttoned sheet 15 and the combination hole 34 of seat block 13 to meet screws 17 and be locked thereby. So packing washers 29, 30 and hole washer 31 seal buttoned sheet 15 from any contact with fluid 8.

Figure 6A:
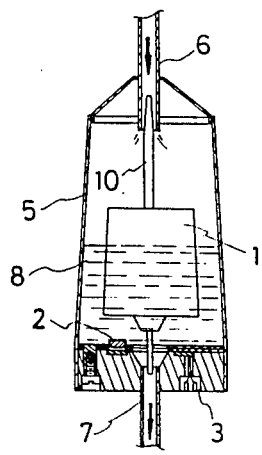
FIGS. 6A and 6B show this invention in operation procedure.
Figure 6B:
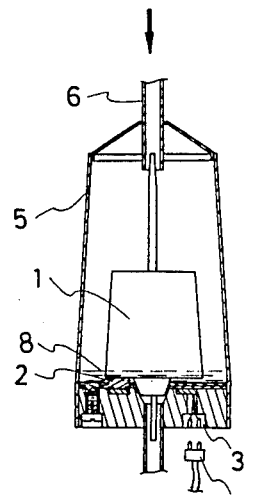

As FIGS. 6A and 6B show, socket 3 is by means of power lead to make connection with copper foil circuits 23 of PC board 14, and is set in a proper location in the seat block 13 bottom part of plugged connection to make with action box 4 or the call assembly of patient room.

Now referring to FIG. 6A, float barrel 1, which stringed between fluid inlet tube 6 and outlet tube 7 in dripping liquid barrel 5, is able to move along with fluid pool 8 vertically up or down, and can maintain fluid pool 8 at preset level by adjusting its inlet flow by means of the upper cone-shaped part of upper guide arm 10. As injection fluid is near depletion (as FIG. 6B shows) and inlet tube 6 has no fluid supply to deliver, fluid pool 8 descends by degrees and float barrel 1 when loosing support of fluid 8 comes down vertically and block outlet tube 7 finally, and at the same time its bottom floor touches touch switch 2, which then conducts on the power source of action box 4 or a call assembly of patient room by way of plug 35 pluggedly connected to socket 3. So alarming signals are caused to send out this way. Action box 4, containing battery, PC board, buzzer, and flasher, after its power source is conducted open will generate sounds and flashes to alert doctors or nurses to come in time. But, since circuits structure of action box 4 is just as used generally and not a characteristic of the invention applying for, no further description is deemed necessary.

FIG. 7 shows how the invention is assembled with dripping injection instruments to be ready for use. By means of fluid inlet tube 6 of dripping liquid barrel 5, fluid 8 streams from a raised, inverted fluid bottle 36 into dripping liquid barrel 5 and float barrel 1 therein therefore rises. Fluid 8, after passing flow requlator 37 and air excluder 38, goes infusing into human body way of needle 39. When injection fluid 8 is going to be used up, float barrel 1 will come down to touch touch switch 2 which in turn by way of power lead conducts open the power source of action box 4 or a call assembly of patient room to bring desired calling effects.

I claim:

1. An alarm device for dripping injection which comprises:

a socket placed in the bottom part of a dripping liquid barrel, having connection to a touch switch;

a plug and power lead connected to said socket from a separate action box or a patient's room call assembly;

a float barrel located between a fluid inlet tube and an outlet tube in the dripping liquid barrel, said float barrel moving up or down vertically and comprising a barrel body with a bottom mid part having stuffing body, an upper guide arm, having stuffing body, and having a lower guide arm; said barrel body having a preset buoyancy in the fluid pool formed in said dripping liquid barrel, said upper guide arm having a cone-shaped upper half connected to said barrel body at its lower half, said said guide arm being inserted into the inlet tube for guiding vertical up or down movement for the barrel body and for adjusting inlet flow of the injection fluid; the bottom mid part of said float barrel provided with said stuffing body and lower guide arm, so that as injection fluid is near empty, said float barrel when loosing support of the fluid pool is guided to descend to accurately block opening of the outlet tube with its stuffing body and, at the same time, the bottom floor of said float barrel touches a touch switch;

said touch switch placed in the lower part of the dripping liquid barrel, comprising a seat block, PC board, a resilient buttoned sheet containing a plurality of buttons, and press sheet; said block which, cylindrical in form, has an outlet and outlet tube provided in the center and, on the upper periphery outside the outlet, has two rings of fillisters provided, and an annular concavity provided therebetween whose dimension is adapted to said PC board for getting it positioned there; said PC board which, annular in form, has at least two copper foil circuits on the board surface, of which any two circuits if closed by a button of said buttoned sheet will cause power source of the action box to be actuated; the buttons on said buttoned sheet which, can take position by the resilient nature of said buttoned sheet, and will be overcome under a proper small amount of pressure to make its touching point in contact with circuits of said PC board thus to have the circuits closed; said buttoned sheet, which is provided with two rings of ridges on the bottom back face in addition to the two rings of fillisters on upper periphery of said seat block, pressed to be engaged with said seat block such that said PC board is sealed entirely away from the injection fluid; said press sheet comprising a touch board which has some holes cut on the board surface in number same as said buttons for them the protrude and has inner and outer packing rings and a hole ring provided on the board back face, combined with said seat block by means of three screw bolts provided on its sheet back face to pass three combination holes provided in said seat block and be locked securely by screws and rendered waterproof; and wherein the alarm device for dripping injection will send out alarming signals automatically as the injection fluid is used up and the fluid level drops allowing said float to move downward to cause said circuits to be closed.

2. A fluid dripping injection alarm device comprising in combination:
a float having a shaped top portion and having a shape bottom portion;
a pressure sensitive switch;
a plurality of circuits;
said shaped top portion comprising means for guiding movement of said float and means for adjusting inlet flow;
said shape bottom portion comprising means for shutting off fluid flow when said fluid is very low and means for guiding said float into contact with said pressure sensitive switch;
said switch having a resilient button whose downward motion is caused by said bottom portion of said float;
wherein two or more of said plurality of circuits are closed by downward motion of said button; and
wherein said switch triggers a lowered fluid level alarm in response to two or more of said plurality of circuits being closed.

* * * * *